United States Patent
Klewinghaus (10) Patent No.: US 12,409,256 B2
(45) Date of Patent: Sep. 9, 2025

(54) COMPUTER SYSTEM FOR SETTING ADJUSTABLE VALUES OF A BLOOD TREATMENT APPARATUS

(71) Applicant: Fresenius Medical Care Deutschland GmbH, Bad Homburg (DE)

(72) Inventor: Juergen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 791 days.

(21) Appl. No.: 17/775,680

(22) PCT Filed: Nov. 12, 2020

(86) PCT No.: PCT/EP2020/081893
§ 371 (c)(1),
(2) Date: Aug. 17, 2022

(87) PCT Pub. No.: WO2021/094446
PCT Pub. Date: May 20, 2021

(65) Prior Publication Data
US 2023/0052003 A1    Feb. 16, 2023

(30) Foreign Application Priority Data

Nov. 12, 2019   (DE) .................... 10 2019 130 433.4

(51) Int. Cl.
| | | |
|---|---|---|
| *A61M 1/16* | (2006.01) | |
| *G16H 20/40* | (2018.01) | |
| *A61M 1/34* | (2006.01) | |

(52) U.S. Cl.
CPC .......... *A61M 1/1601* (2014.02); *G16H 20/40* (2018.01); *A61M 1/341* (2014.02)

(58) Field of Classification Search
CPC .............. A61M 1/1613; A61M 1/1615; A61M 1/1601; A61M 1/341
See application file for complete search history.

(56) References Cited

U.S. PATENT DOCUMENTS

| | | |
|---|---|---|
| 8,900,172 B2 | 12/2014 | Pohlmeier |
| 9,022,966 B2 | 5/2015 | Lannoy |
| (Continued) | | |

FOREIGN PATENT DOCUMENTS

| | | |
|---|---|---|
| DE | 102011010406 | 8/2012 |
| DE | 102013001587 | 7/2014 |
| (Continued) | | |

OTHER PUBLICATIONS

International Search Report and Written Opinion in International Appln. No. PCT/EP2020/081893, mailed Feb. 19, 2021, 21 pages (with English translation).

*Primary Examiner* — Guy K Townsend
*Assistant Examiner* — Peter Daniel Smith
(74) *Attorney, Agent, or Firm* — Fish & Richardson P.C.

(57) ABSTRACT

A computer system for setting adjustment values of a blood treatment apparatus includes a first input interface, a second input interface, an output interface, a display device, and a calculation device. The calculation device is programmed, after reading a target value for the renal dose via a blood treatment apparatus, to display to the user in a graphic via the display device, a selection range from several combinations, each of one adjustable value for the flow of the blood pump and one adjustable value for the flow of the dialysis liquid pump. Based on the displayed selection range, the user can select one of the displayed combinations via the second input interface. The calculation device is further programmed so that the adjustable value for the blood pump and the adjustable value for the dialysis liquid pump of the selected combination can be given via the output interface.

15 Claims, 4 Drawing Sheets

(56) References Cited

U.S. PATENT DOCUMENTS

| | | |
|---|---|---|
| 9,278,171 B2 | 3/2016 | Brandl et al. |
| 10,307,526 B2 | 6/2019 | Heide et al. |
| 2003/0029797 A1* | 2/2003 | Govoni ............... A61M 1/1613 |
| | | 210/321.71 |
| 2010/0042035 A1* | 2/2010 | Moissl ................ A61M 1/1615 |
| | | 210/321.71 |
| 2015/0374897 A1 | 12/2015 | Favre |
| 2017/0326284 A1 | 11/2017 | Dulsner et al. |
| 2018/0110916 A1 | 4/2018 | Xue |
| 2018/0147335 A1 | 5/2018 | Nilsson |
| 2018/0361045 A1 | 12/2018 | Griessmann |

FOREIGN PATENT DOCUMENTS

| | | |
|---|---|---|
| DE | 102014113462 | 3/2016 |
| DE | 102019130433 A1 | 5/2021 |
| EP | 2564885 | 3/2013 |
| EP | 2762179 | 8/2014 |
| EP | 2959928 | 12/2015 |
| EP | 3416073 | 12/2018 |
| WO | WO 2009/026603 | 3/2009 |
| WO | WO 2010/148194 | 12/2010 |

\* cited by examiner

COMPUTER SYSTEM FOR SETTING ADJUSTABLE VALUES OF A BLOOD TREATMENT APPARATUS

CROSS-REFERENCE TO RELATED APPLICATIONS

The present application is the national stage entry of International Patent Application No. PCT/EP2020/081893, filed on Nov. 12, 2020, and claims priority to Application No. 10 2019 130 433.4, filed in the Federal Republic of Germany on Nov. 12, 2019, the disclosures of which are expressly incorporated herein in its entirety by reference thereto.

FIELD OF THE DISCLOSURE

The present disclosure relates to a computer system. It also relates to a blood treatment apparatus and a system according to the present disclosure. It also relates to a method, a digital storage medium, a computer program product, and a computer program according to the present disclosure.

BACKGROUND

For the purpose of the blood treatment, adjustable values for variable treatment parameters are entered by a user, for example the hospital staff, on the blood treatment apparatus used for this purpose. The user can change such adjustable values by manual input, e.g., via a screen (touch screen) or other interfaces.

In order to achieve predetermined treatment goals or predetermined targets, such as the renal dose in dialysis treatment, it may be necessary for the user to determine or change a series of adjustable values which are in part interrelated, which is why setting the blood treatment apparatus can be a demanding and error-prone activity.

SUMMARY

An object of the present disclosure may also consist of proposing a computer system to assist the user in setting (or specifying, or determining or fixing hereafter referred to as setting), adjustable values of a blood treatment apparatus, also a blood treatment apparatus which includes a computer system according to the present disclosure, a system and a method. Furthermore, a digital storage medium, a computer program product and a computer program shall be proposed.

The object according to the present disclosure may be achieved by a computer system having the features of the present disclosure. It may be further achieved by a blood treatment apparatus having the features of the present disclosure as well as a system having the features of the present disclosure, furthermore by a method having the features of the present disclosure. It may further be achieved by a digital storage medium having the features of the present disclosure, by a computer program product having the features of the present disclosure as well as by a computer program having the features of the present disclosure.

The computer system according to the present disclosure helps the user (physician, personnel, etc.) to set adjustable values for their later use on the blood treatment apparatus and thereby supports them. It includes at least a first input interface, a second input interface as well as an output interface. It further includes a calculation (or computing device) and a display device or is connected to the above interfaces in signal communication.

The calculation device is programmed to use the first input interface to read a target value, which can also be a target range, here exemplarily the renal dose, as a parameter value for a subsequent or future patient's treatment using a blood treatment apparatus.

Furthermore, the calculation device is programmed to display to a user via the display device a selection range calculated by the calculation device, preferably in a graphic.

Thereby, the selection range is determined by the calculation device taking into account the read target value of the renal dose. For example, the selection range can be used to display a plurality of combinations of or with exactly one adjustable value for the flow of the blood pump on the one hand and exactly one adjustable value for the flow of the dialysis liquid pump on the other. These adjustment ranges, should they be set on the blood treatment apparatus, allow (ceteris paribus) the achievement of the target value according to the information available to the calculation device.

Using a second input interface, the user can select one, preferably any one of the combinations displayed.

The calculation device is therefore further programmed to give, via the output interface, the adjustable value for the blood pump and the adjustable value for the dialysis liquid pump of the selected combination.

The blood treatment apparatus according to the present disclosure is embodied as a dialysis apparatus, which includes a computer system according to the present disclosure.

The system according to the present disclosure includes one or several blood treatment apparatuses and a computer system according to the present disclosure or consists of such.

Thereby, the blood treatment apparatus is preferably embodied as a dialysis apparatus.

The one or more blood treatment apparatus(es) and the computer system are separate from one another. The term "separate" may encompass, for example, a spatial, physical separation and/or a separation in such that there is no signal communication between the blood treatment apparatus and the computer system.

The method according to the present disclosure for setting adjustable values of a blood treatment apparatus (or assisting e.g., the medical personnel in finding or setting appropriate adjustable values) encompasses the following steps:

a. providing a computer system according to the present disclosure, a blood treatment apparatus according to the present disclosure or a system according to the present disclosure;

b. reading a target value and/or a target range for a parameter value, e.g., for the renal dose, for a patient's subsequent treatment via a blood treatment apparatus, preferably after completion of the method according to the present disclosure, or entering these parameters via a first input interface; the first input interface may be also be optionally used as an reading interface;

c. displaying a selection range of combinations of adjustable values calculated or determined by the calculation device, wherein the displaying is done via the display device, for example in a graphic, e.g., in a diagram;

d. selection by the user via a second input interface of one of the combinations displayed via the selection range; and e. Giving the adjustable value for the blood pump and the adjustable value for the dialysis liquid pump of the selected combination via the output interface.

Anything referred to previously or in the following regarding the computer system according to the present disclosure or its features applies analogously without limitation to the method according to the present disclosure or its possible embodiments and vice versa. Therefore, to avoid repetition, reference is hereby made to statements and definitions made about the same subject-matter or term at any other place herein.

A digital, non-volatile storage medium, according to the present disclosure, such as in the form of a machine readable medium, such as in the form of a diskette, CD, DVD EPROM, FRAM (Ferroelectric RAM) or SSD (Solid-State-Drive), such as with electronically or optically readable control signals, can be configured or programmed to interact with a programmable computer system, so that a computer system can be programmed to be a computer system according to the present disclosure, e.g., if its memory content runs on the programmable computer system.

A computer program product, according to the present disclosure, includes a volatile or transient, or stored on a machine-readable carrier, program code or a signal wave, configured to interact in such a way with a programmable computer configuration of a computer system so that the computer system can be reprogrammed to be a computer system according to the present disclosure. Computer program product, may be understood according to the present disclosure, for example, as a computer program stored on a carrier, an Embedded System being a comprehensive system with a computer program (e.g., electronic device with a computer program), a network of computer implemented computer programs (e.g., client/server-system, a cloud computing system etc.), or a computer on which a computer program is loaded, runs, is stored, is executed or developed.

The term "machine-readable carrier" as is as used herein, refers in certain embodiments of the present disclosure to a medium, which contains data or information interpretable by software and/or hardware. The carrier may be a data carrier, such as a diskette, a CD, DVD, a USB stick, a flashcard, an SD card or the like, as well as any other storage referred to herein or any other storage medium referred to herein.

According to the present disclosure, a computer program product can also be understood to mean a programmed application (in short: app), for example, such as for a smartphone, a tablet or any another mobile handheld device. A computer program according to the present disclosure includes a program code to cause a computer system to be reprogrammed into a computer system according to the present disclosure, when the computer program runs on a corresponding computer system. According to the present disclosure, a computer program can be understood to mean, for example, a physical, ready-for-distribution software product that has a program.

In all of the following statements, the use of the expression "may be" or "may have" and so on, is to be understood synonymously with "preferably is" or "preferably has," and so on respectively, and is intended to illustrate embodiments according to the present disclosure.

Embodiments according to the present disclosure may include one or several of the aforementioned or following features. In this, the features mentioned herein may, in any combination, be subject-matter of embodiments according to the present disclosure, unless the person skilled in the art recognizes a specific combination as technically impossible.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" as encompassing "at least one". This understanding is also equally encompassed by the present disclosure as the interpretation that a numeric word, for example, "one" may alternatively mean "exactly one", wherever this is evidently technically possible for the person skilled in the art. Both are encompassed by the present disclosure and apply herein to all used numerical words.

Whenever an applicability or a method step is mentioned herein, the present disclosure also preferably encompasses a corresponding programming or configuring of a suitable apparatus or a section thereof.

Whenever an embodiment is mentioned herein, it is then an exemplary embodiment according to the present disclosure.

The statements "top" and "bottom" are to be understood here in case of doubt by the person skilled in the art as absolute or relative spatial indications, which relate to the orientation of the relevant component during its intended use.

The selection range may be smaller than the technically possible and/or total combinations displayed in the graph.

Selecting from the combinations displayed via the selection range can also be a marking, for example using a computer mouse. Selecting can optionally include moving an already marked value or an already marked combination to a new value or to a new combination.

The first and/or the second input interface can respectively be a correspondingly embodied touch screen, a rotary switch, a slider, a keyboard or the like.

The first input interface and the second input interface can be identical, i.e. they can be realised by only one common input interface. Alternatively thereto, they can be different and/or independent of each other.

The target value or range can be taken into account when determining or calculating the adjustable values of the selection range, e.g., based on known algorithms, which in turn can include further parameter values, e.g., from auxiliary tables etc. These algorithms and/or further parameter values (as well as further adjustable values corresponding to the latter) can be stored, for example, in a storage device of the computer system.

The target value can be entered by the user or can be read out by the calculation device via its first interface, which may be, for example, an interface to a storage device.

The target value can relate to the specific patient to be treated.

A renal dose may be set as a quotient of effluent flow or filtrate flow on the one hand and patient weight on the other hand.

When determining the effluent flow, different flows (e.g., dialysate flow, substitute flow, calcium flow, citrate flow, net ultrafiltration) may have to be taken into account, depending on the type of therapy.

The renal dose may be, for example, the target renal dose (TRD) or the effective renal dose (RRD).

The target renal dose (TRD) may be calculated for example, by using the following formula:

$$TRD = \frac{PostDF + DF + NFRF + \frac{PreDF}{1 + \frac{PreDF}{BF}}}{m}$$

The following applies here:
BF blood flow rate
DF dialysis liquid flow rate
NFRF net liquid removal flow rate
m patient's weight
PostDF post-dilution flow rate
PreDF pre-dilution flow rate.

The effective renal dose (RRD) can be calculated, depending on the duration of therapy t, using the formula:

$$RRD = \frac{\frac{PostDV}{t} + \frac{DV}{t} + \frac{NFRV}{t} + \frac{\frac{PreDV}{t}}{1 + \frac{t}{\frac{BV}{t}}}}{m}$$

wherein applies:
BV processed blood volume
DV dialysis liquid volume
NFRV net liquid removal volume
m patient's weight
PostDV post-dilution volume
PreDV pre-dilution volume In some embodiments, the calculation device of the computer system is programmed in such a way that it is able to read further parameter values e.g., the same or another parameter, and to further limit, segment, subdivide or classify the selection range of the possible adjustable values based on these parameter values. These additional parameter values can be read in the same way as the target value.

In several embodiments, the further parameters or parameter values take into account or consideration a desired anticoagulation for or during the treatment, such as a citrate-calcium anticoagulation, or a desired bicarbonate concentration, e.g., in the serum.

In some embodiments, the computer system is or includes a mobile device. It can be or include a handheld device, cell phone, smartphone, tablet or the like.

In several embodiments, the computer system encompasses a computer program or an application (in short: app) which can be loaded onto just such a mobile device or other device, or is stored, can be executed on or is running on such a device.

In several embodiments, the calculation device of the computer system is programmed to display, for the attention of the user via the display device, the adjustable value for the blood pump and the adjustable value for the dialysis liquid pump of the selected combination and/or, via the output interface, for example, to give it to a control device or closed-loop control device of a blood treatment apparatus. This in turn can read in and/or store the transmitted adjustable values.

The transmitted adjustable settings can be used by the blood treatment device for an upcoming treatment session.

In some embodiments, the output interface and display device may be identical. An output via the output interface can therefore be a displaying using the display device, and vice versa.

In several embodiments, the computer system according to the present disclosure is programmed to give, e.g., via the aforementioned output interface, values that indicate set flows and/or the renal dose, such as the target value for the renal dose and/or the actual flows or the adjustable values for the pumps mentioned herein, e.g., the blood pump, the dialysis liquid pump, the substituate pump, the calcium pump, the citrate pump, the Heparin pump and/or other pumps.

The computer system can be programmed, for example, to transfer these values to a logistics system and/or an invoicing system. The logistics system and/or an invoicing system, which may be provided outside of the computer system but nevertheless can be part of the system according to the present disclosure, can in turn be programmed to monitor, record, store, output, invoice, charge and/or in any other way process delivery flows, orders, consumption and the like. Therefore, the logistics system can be configured to use the values transmitted by the computer system to reorder fluids used during a blood treatment session, such as citrate solution, dialysis liquid, etc. and initiate their delivery to the clinic in which the blood treatment was carried out. The invoicing system can use the values transmitted by the computer system to bill the services in connection with the blood treatment session which the clinic has rendered. For example, the target value of the renal dose or the value, such as the Heparin flow, that reflects the consumption of liquids such as Heparin, citrate solution etc. can be used as the basis for billing the patient or a cost bearer such as an insurance company.

In some embodiments, the computer system according to the present disclosure is a control device or closed-loop control device of a blood treatment apparatus or is in signal communication with such a device.

According to the present disclosure, it may also be provided in some embodiments that the computer system according to the present disclosure is implemented in a control device or closed-loop control device of a, for example, conventional blood treatment apparatus, whereby the blood treatment apparatus would in turn be configured into a blood treatment apparatus according to the present disclosure. In these embodiments, existing input and output interfaces as well as the calculation device of the blood treatment apparatus could then be advantageously used to implement the computer system according to the present disclosure.

In several embodiments, the computer system may be or include a server-based solution wherein the user can, via a web site, for example, access a program running on the server in order to run or initiate the steps of the method according to the present disclosure. The computer system can therefore optionally include a server. It can include user interfaces and/or user devices such as computers, cell phones or tablets, which are set up to communicate with the server.

In some embodiments, the control device or closed-loop control device is programmed to control or regulate the blood treatment apparatus based on adjustable value for the blood pump and the adjustable value for the dialysis liquid pump according to the selected combination, such as after selection has been made.

In several embodiments the blood treatment apparatus according to the present disclosure is embodied as a hemodialysis apparatus, hemofiltration apparatus or hemodiafiltration apparatus, such as an apparatus for the chronic, the acute or for the continuous renal replacement therapy (CRRT).

In some embodiments, the method according to the present disclosure includes as a further step displaying or giving the adjustable value for the blood pump and the adjustable value for the dialysis liquid pump of the selected combination. The displaying or outputting can optionally be carried out via a display device for the attention of and/or confirmation by the user.

The confirmation may simply be the operation of an "OK" button or the like

Confirmation, in some embodiments, does not encompass typing, entering, selecting, etc. of adjustable values from a variety of options, or doing it by mental arithmetic.

In several embodiments, the method according to the present disclosure encompasses as a further step the, preferably automatic, controlling or regulating of a blood treatment apparatus based on the adjustable value for the blood pump and on the adjustable value for the dialysis liquid pump of the selected combination.

This can, for example, directly follow the selection, or a confirmation of the selection made by the user.

In some embodiments, the method according to the disclosure includes, as a further step, reading the adjustable value for the blood pump and the adjustable value for the dialysis fluid pump of the selected combination into a memory (this can, for example, be volatile or permanent), e.g., the blood treatment device, for a subsequent treatment or one which is yet to begin or treatment session via the blood treatment device.

Further parameter values can be or relate to the acid/base balance of the patient or the composition of his blood.

Whenever "programmed" or "configured" is mentioned herein, it is to be understood that these terms are interchangeable.

Several or all embodiments according to the present disclosure may include one, more or all of the advantages mentioned above and/or in the following.

An advantage of the present disclosure may be to aid or make the decision easier for the user, i.e. usually the attending physician, as to which adjustable values may be selected for blood treatment apparatus pumps for the upcoming or current blood treatment in order to be able to achieve a predetermined target value during the treatment with them, which at the same time is not a target adjustable value of one of the pumps. As using the disclosure, in view of the target value, rules out from the start unfavorable combinations from the numerous possible combinations, this considerably reduces the complexity of the decision-making task for the physician.

A further advantage of the present disclosure can be that changing the adjustable values using the simplification according to the present disclosure can also advantageously give the less experienced user more certainty when carrying out the adjusting.

The possibility of making an error when finding adjustable values can be, according to the present disclosure, significantly reduced, for example, because mental arithmetic steps and/or the risk of errors such as a human error made by the user can be eliminated.

This means that indirectly the patient's safety can advantageously be improved.

The competence and responsibility for finding or changing the adjustable values, can, however, advantageously remain with the user. The user thus receives valuable support from the computer system according to the present disclosure, but without being surprised by its acting without authorization.

If the blood treatment apparatus and the computer system remain separate devices, existing blood treatment apparatuses may be combined with the computer system according to the present disclosure to form the system according to the present disclosure. Since interventions in the control of the blood treatment apparatus are not necessary, the blood treatment apparatus does not need to be re-approved as a medical device.

BRIEF DESCRIPTION OF THE FIGURES

The present disclosure is exemplarily explained with regard to the accompanying drawings in which same reference numerals refer to the same or similar elements. In the figures of the drawing the following applies.

DETAILED DESCRIPTION

Figure 1:
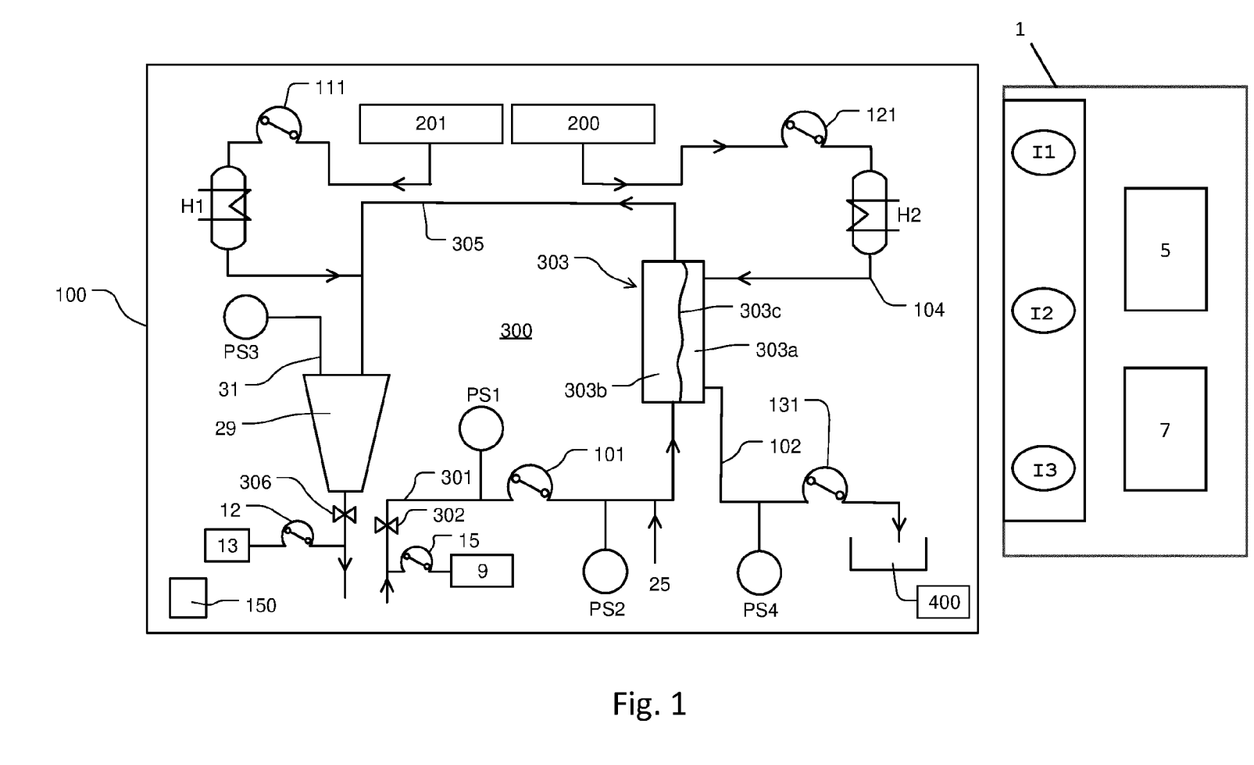
FIG. 1 shows in a highly simplified representation, a system according to the present disclosure having a blood treatment apparatus next to a computer system according to the present disclosure.

FIG. 1 shows in highly simplified representation a blood treatment apparatus 100, optionally connected to an extracorporeal blood circuit 300, as part of a system according to the present disclosure.

The extracorporeal blood circuit 300 includes a first line 301, here in the form of an arterial line section.

The first line 301 is in fluid connection with a blood treatment device, here exemplarily, a blood filter or dialyzer 303. The blood filter 303 includes a dialysis liquid chamber 303a and a blood chamber 303b, which are separated from each other by a mostly semi-permeable membrane 303c.

The extracorporeal blood circuit 300 further includes at least one second line 305, here in the form of a venous line section. Both the first line 301 as well as the second line 305, can serve to be connected to the vascular system of the patient, not shown.

The first line 301 is optionally connected to a (first) tube clamp 302 for blocking or closing the line 301. The second line 305 is optionally connected to a (second) tube clamp 306 for blocking or closing the line 305.

The blood treatment apparatus 100 represented in FIG. 1 schematically and only by some of its devices, includes a blood pump 101. During the patient's treatment the blood pump 101 conveys blood through sections of the extracorporeal blood circuit 300 and towards the blood filter or dialyzer 303 as shown by the small arrows, which generally indicate the direction of flow in each of the figures. Using a pump for dialysis liquid 121, that may be embodied as a roller pump or as any otherwise occluding pump, fresh dialysis liquid is pumped from a source 200 along the dialysis liquid inlet line 104 into the dialysis liquid chamber 303a. The dialysis liquid leaves the dialysis liquid chamber 303a as dialysate, possibly enriched with filtrate, towards an optional effluent bag 400 and will be referred to herein as effluent.

The source 200 may, for example, be a bag or a container. The source 200 may further be a fluid line from which on-line and/or continuously produced or mixed liquid is provided, for example, a hydraulic outlet or hydraulic port of the blood treatment apparatus 100.

A further source 201 with substitute may optionally be provided. It may correspond to the source 200 or be a separate source.

A control device or closed-loop control device 150, only shown schematically can be configured to control or regulate the blood treatment session.

Where the effluent bag 400 is connected to the blood treatment apparatus 100b is indicated in the bottom right of FIG. 1.

In addition to the aforementioned blood pump 101, the arrangement shown in FIG. 1 further includes, purely optionally, a number of other optional pumps, namely the pump 111 for substitute, the pump 121 for dialysis liquid and the pump 131 for the effluent.

The pump 121 is provided to supply dialysis liquid out of a source 200, for example a bag, through an optionally available bag heater H2 having a heat bag, to the blood filter 303 using the dialysis liquid inlet line 104.

The thus supplied dialysis liquid exits again from the blood filter 303 via a dialysate outlet line 102, aided by the optional pump 131, and may be discarded.

An optional arterial sensor PS1 is provided upstream of the blood pump 101. It measures the pressure in the arterial line during a patient's treatment.

A further optional pressure sensor PS2 is provided downstream of the blood pump 101, but upstream of the blood filter 303 and if provided, upstream of an addition point 25 for Heparin. It measures the pressure upstream of the blood filter 303 ("pre-hemofilter").

To measure the filtrate pressure of the blood filter 303 again a further pressure sensor may be provided as PS4 downstream of the blood filter 303, however, preferably upstream of the pump 131 in the dialysate outlet line 102.

Blood, which leaves the blood filter 303, passes through an optional venous blood chamber 29, which may include a ventilation device 31 (also: venting; de-aeration or de-airing device) and/or a further pressure sensor PS3.

The control device or closed-loop control device 150 shown in FIG. 1 may be in wired or wireless signal communication to any of the components referred to herein—such as or at least to the blood pump 101—in order to control or regulate the blood treatment apparatus 100.

The optional pump 111 is provided to supply substitute out of the optional source 201, for example a bag, via an optional available bag heater H1 having a heat bag, to the second line 305.

In several embodiments a citrate solution is dispensed from an optionally provided source for citrate solution, here exemplarily embodied as a citrate bag 9, into the first line 301, possibly by a citrate pump 15. For example, 4%-Na$_3$Citrate is added from the citrate solution source.

An optional addition device, embodied herein as calcium pump 12, is provided to supply a calcium solution from an optional source for calcium solution, exemplarily embodied in FIG. 1 as a calcium bag 13, into the line 305. For example, a CaCl$_2$— solution is supplied from the source of calcium solution. This may have a calcium concentration of 91 mmol/l, 100 mmol/l, or another suitable calcium concentration.

In FIG. 1 to the right of the blood treatment apparatus 100, a computer system 1 according to the present disclosure is illustrated having a calculation device 5 and an optional storage device 7. The computer system has a first input interface I1 and a second input interface 12 and an output interface 13.

Blood treatment apparatus 100 and computer system 1 together represent an embodiment of a system according to the present disclosure.

The computer system 1 can be provided on a mobile hand-held device, for example a cell phone or tablet, physically separated from the blood treatment apparatus 100. In the embodiment shown in FIG. 1, it is not connected to the blood treatment apparatus 100 in signal communication.

The computer system 1 can be or include a server-based solution where the user, for example, can access, via a website, a program running on the server in order to run or initiate the steps of the method according to the present disclosure. The computer system 1 can therefore include a server. It may include user interfaces and/or user devices such as computers, cell phones or tablets which are set up to communicate with the server.

However, in other embodiments of the blood treatment apparatus than those shown here, the computer system is connected in signal communication and/or physically to the blood treatment apparatus 100 or is a part thereof. In the latter, however, the devices connected in this way no longer relate to a system according to the present disclosure, but rather to a blood treatment apparatus according to the present disclosure.

It is also encompassed by the present disclosure that the computer system 1, differently than as it is shown here, is identical to or is encompassed by the control device or closed-loop control device 150.

Figure 2:
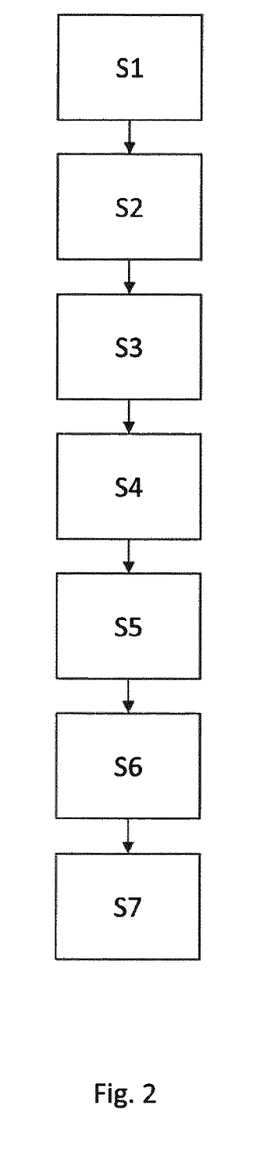
FIG. 2 shows a flow chart of an exemplary embodiment of the method according to the present disclosure.

FIG. 2 shows a flow chart of an exemplary embodiment of the method according to the present disclosure Therein, the method step S1 shows the provision of a computer system 1 according to the present disclosure, a blood treatment apparatus 100 according to the present disclosure or a system according to the present disclosure.

In method step S2 a target value and/or a target range is read for a parameter value for a patient's treatment, for example for a renal dose, using a blood treatment apparatus 100 or this parameter value is entered via a first input interface I1.

S3 represents the displaying, of a selection range (see reference numeral A in FIG. 3b), calculated by the calculation device (5), for example as described supra, via the display device (I3), for example in a graphic, e.g., a diagram.

Figure 3A:
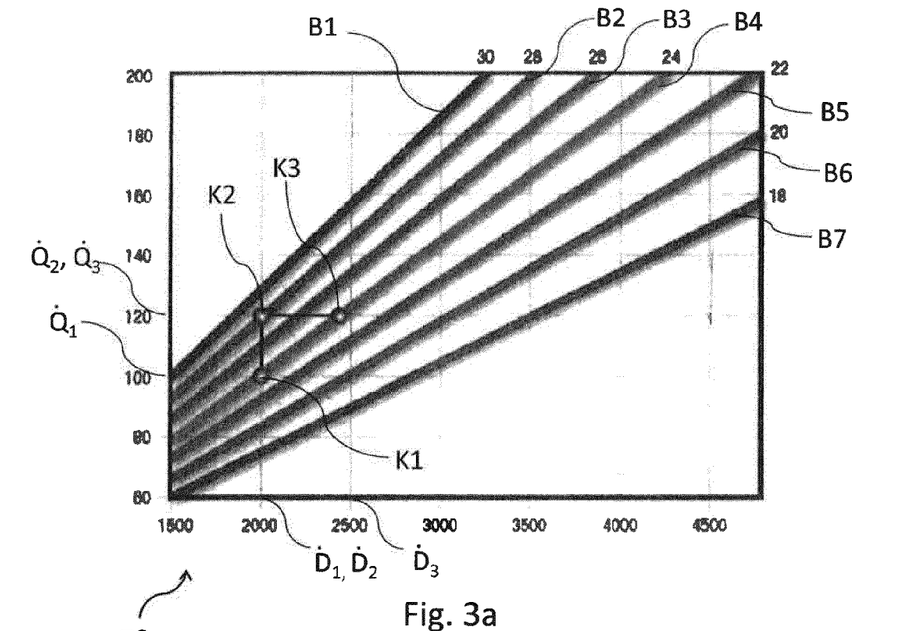
FIG. 3a shows parts of a graphic (or graphic display) as it could be displayed to the user via the display device in an exemplary embodiment of the computer system according to the present disclosure or the method according to the present disclosure.
Figure 3B:
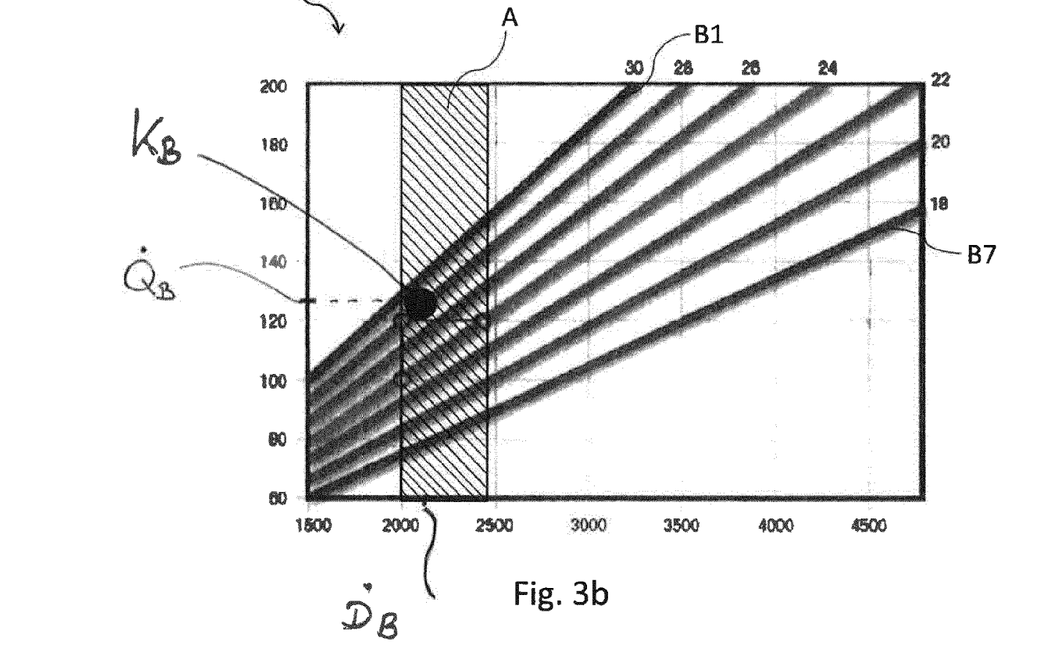
FIG. 3b shows the graphic of FIG. 3a with a marked selection range for new adjustable values.

In method step S4, one of the displayed combinations is selected by the user using a second input interface 12, which can optionally be identical to the first input interface, as shown in FIG. 3b.

In the method step S5, the adjustable value for the blood pump 101 and the adjustable value for the dialysis liquid pump 121 of the selected combination are given via the output interface.

Optionally, in method step S6, the adjustable value for the blood pump 101 and the adjustable value for the dialysis liquid pump 121 of the selected combination are displayed or given via the display device 13 so that the user can take note of them.

S7 represents the optional method step of controlling or regulating the blood treatment apparatus 100 based on the adjustable value for the blood pump 101 and on the adjustable value for the dialysis liquid pump 121 of the selected combination.

FIG. 3a shows essential parts of a graphic or graphical display as it could be displayed to the user via the display device 13 in an exemplary embodiment of the computer system or in an exemplary embodiment of the method.

In the diagram of the graphical display, the vertical axis represents the blood flow [in ml/min] over the dialysis liquid flow [in ml/h] on the horizontal axis.

Each point within the diagram shown thus corresponds on the one hand to a combination of a possible adjustable value $Q;\dot{}_n$ for the delivery rate for the blood pump and a possible adjustable value $\dot{D}_n$ for the delivery rate of the dialysis liquid pump on the other. So, for example, the combination K1 corresponds to a combination of 100 ml/min as the rate for the blood pump (adjustable value $Q;\dot{}_1=100$ ml/min) of 2000 ml/min as the rate for the dialysis liquid pump (adjustable value $\dot{D}_1=2000$ ml/min). The combination K2 however stands for 120 ml/min as the rate for the blood pump (adjustable value $Q;\dot{}_2=120$ ml/min) of—as already in combination K1—2000 ml/min as the rate for the dialysis liquid pump (adjustable value $\dot{D}_2=2000$ ml/min).

The possible setting of a number of such combinations K1, K2, K3, . . . of a delivery rate for the blood pump and a delivery rate for the dialysis liquid pump, mathematically results in an expected acid-base status (expected (or anticipated)) bicarbonate concentration in the serum).

The expected bicarbonate concentrations in the serum are shown for a number of combinations of blood flow rate and dialysis fluid flow rate in each case in the form of a ray in the diagram. The lines shown are designated B1 to B7. For each of them, the value (in mmol/l) of bicarbonate to be expected is given on the edge of the diagram, when setting a combination of flows lying on the rays (the values of the graph in FIG. 3a were determined in a simulation).

In the present example it could be seen that an increase in blood flow of 20%, from K1 to K2, alters the expected bicarbonate concentration in the serum by about 4 mmol/l (from 24 mmol/l to 28 mmol/l, i.e. towards metabolic alkalosis). An increase in dialysate flow of also 20% (to K3) would compensate this effect.

The underlying constant treatment parameters in this example are: citrate dose 4 mmol per litre of blood, calcium dose 1.7 mmol per litre of blood, net ultrafiltration 100 ml/h.

ß The selection range which is available to the user according to the present disclosure is for the sake of clarity, not shown in FIG. 3a. It is indicated by the reference numeral A in FIG. 3b and FIG. 3c.

FIG. 3b FIG. 3 shows the exemplary graphic or graphical display of FIG. 3a.

All statements for FIG. 3a therefore also apply to FIG. 3b.

Illustrated here in FIG. 3b is a selection range A with an indefinite number n of possible combinations of adjustable values $Q;\dot{}_n$ for the delivery rate of the blood pump and adjustable values $\dot{D}_n$ for the delivery rate of the dialysis liquid pump.

The selection range A visually highlights the combinations from the n possible combinations in which the associated adjustable values are suitable for being set on the blood treatment apparatus 100, in order to achieve the target value, i.e. for the renal dose, during or with the treatment carried out with them. The combinations marked by selection range A are thus selected or determined taking into account the target value for the renal dose.

In the example in FIG. 3b, the selection range A is marked by shading. It does not have to be shaded as shown in FIG. 3b, but can also be highlighted in other ways. Coloured backgrounds are also possible. Its shape can of course also differ from the bar shape shown here.

Purely as an example, it is assumed in FIG. 3b that the user has decided on a combination of $K_B$, e.g., by marking it using the computer mouse, which should be illustrated by the circle within the selection range A. The adjustable values $Q;\dot{}_B$ for the delivery rate of the blood pump and $\dot{D}_B$ for the delivery rate of the dialysis liquid pump attributed to this combination $K_B$ can be displayed to the user, optionally with an indication of the exact adjustable values in for example ml/min. Provision may be made for a confirmation by the user before the blood treatment apparatus takes any action based thereon.

A treatment using the adjustable values $Q;\dot{}_B$ $\dot{D}_B$, however, allows a treatment which obtains the desired renal dose, i.e. the target value.

The displaying or highlighting of the selected combination $K_B$ may correspond to an output via the output interface and/or a display via the display device.

Figure 3C:
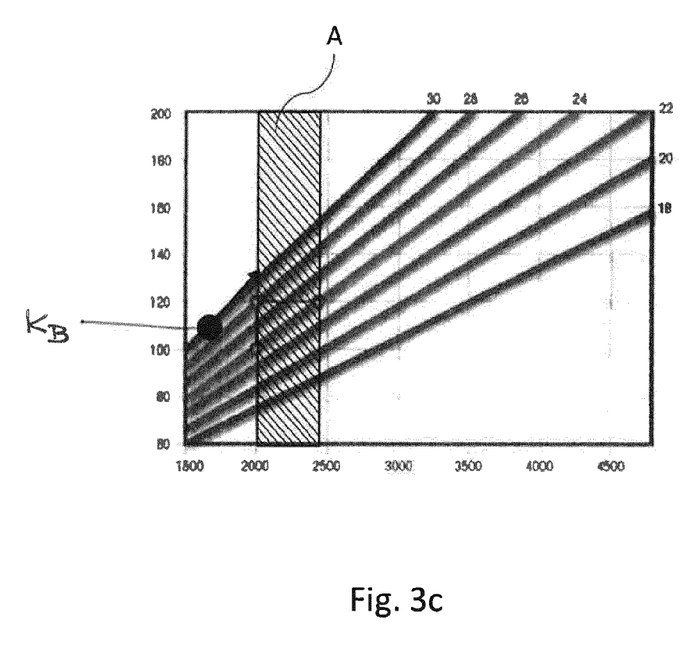
FIG. 3c shows the graphic of FIG. 3b during a setting procedure.

FIG. 3c In contrast to the representation in FIG. 3b, however, the user has selected a combination $K_B$ which lies outside the selection range A. The adjustable values of this combination are not suitable in order to reach the target value for the renal dose when carrying out a blood treatment with them.

The user can be made aware of this optionally via a warning, indication or the like. He may have the opportunity to correct his selection and move the first selected combination $K_B$ into the selection range A. If he follows the arrow shown in FIG. 3c, he would maintain the desired bicarbonate concentration.

LIST OF REFERENCE NUMERALS 1 computer system
5 calculation device (or computing device)
7 storage device (optional)
9 source for citrate solution, here, e.g., a citrate bag
12 calcium pump
13 source for calcium solution, calcium bag
15 citrate pump
25 addition point for Heparin (optional)
29 venous blood chamber (optional)
31 ventilation (or venting, de-aeration or de-airing device)
100 blood treatment apparatus
101 blood pump
102 dialysate outlet line, effluent inlet line
104 dialysis liquid inlet line
111 pump for substituate
121 pump for dialysis liquid
131 pump for dialysate or effluent in effluent inlet line
150 control device or closed-loop control device
200 dialysis liquid source
201 substituate source, optional
300 extracorporeal blood circuit
301 first line (arterial line section)
302 (first) tube clamp
303 blood filter or dialyzer
303a dialysis liquid chamber
303b blood chamber
303c semi-permeable membrane
305 second line (venous line section)
306 (second) tube clamp
A selection range
I1 first input interface
I2 second input interface
I3 display device
K1 combination 1
K2 combination 2
K3 combination 3
$K_B$ selected combination
B1 expected (or anticipated) bicarbonate concentration in serum of 30 mmol/l B2 expected bicarbonate concentration in serum of 28 mmol/l
B3 expected bicarbonate concentration in serum of 26 mmol/l
B4 erwartete Bicarbonatkonzentration im Serum of 24 mmol/l
B5 erwartete Bicarbonatkonzentration im Serum of 22 mmol/l
B6 erwartete Bicarbonatkonzentration im Serum of 20 mmol/l
B7 erwartete Bicarbonatkonzentration im Serum of 18 mmol/l
S1 method step a
S2 method step b
S3 method step c
S4 method step d
S5 method step e
S6 further method step
S7 further method step
$Q{;}_1^*$, $Q{;}_2^*$, $Q{;}_3^*$, $Q{;}_B^*$ adjustable values for the blood pump
$\dot{D}_1$, $\dot{D}_2$, $\dot{D}_3$, $\dot{D}_B$ adjustable values for the dialysis liquid pump

The invention claimed is:

1. A computer system to set adjustable values of a blood treatment apparatus, the computer system comprising:
a first input interface;
a second input interface;
an output interface; and
a display device;
a calculation device programmed to:
use the first input interface to read a target value of a renal dose as a parameter value for a treatment of a patient using the blood treatment apparatus in order to display to a user in a graphic, via the display device, a selection range that is determined by the calculation device taking into account a read target value of the renal dose and a plurality of combinations of one adjustable value for a flow of a blood pump and one adjustable value for a flow of a dialysis liquid pump, wherein the second input interface is used to select a combination from the plurality of combinations displayed by the user; and
give the adjustable value for the blood pump and the adjustable value for the dialysis liquid pump of a selected combination via the output interface.

2. The computer system according to claim 1, wherein the calculation device is further programmed to read further parameter values, wherein the selection range is further restricted by the calculation device taking into account the further parameter values.

3. The computer system according to claim 2, wherein the further parameter values take into account a desired anticoagulation or a desired bicarbonate concentration in the serum.

4. The computer system according to claim 3, wherein the desired anticoagulation comprises a citrate-calcium anticoagulation.

5. The computer system according to claim 1, wherein the computer system is a mobile device, a hand-held device, a cell phone, a smartphone, a tablet, or another application.

6. The computer system according to claim 1, wherein the calculation device is programmed to display for attention of the user the adjustable value for the blood pump and the adjustable value for the dialysis liquid pump of the selected combination.

7. The computer system according claim 1, wherein the computer system is a control device of the blood treatment apparatus or is in signal communication with the blood treatment apparatus.

8. The computer system according to claim 7, wherein the control device is programmed to control or regulate the blood treatment apparatus based on the adjustable value for the blood pump and the adjustable value for the dialysis liquid pump of the selected combination.

9. The computer system according to claim 7, wherein the control device comprises a closed-loop control device.

10. A dialysis apparatus comprising a computer system for setting adjustable values of the dialysis apparatus, the computer system comprising:
a first input interface;
a second input interface;
an output interface; and
a display device;
a calculation device programmed to:
use the first input interface to read a target value of a renal dose as a parameter value for a treatment of a patient using the dialysis apparatus in order to display to a user in a graphic, via the display device, a selection range that is determined by the calculation device taking into account a read target value of the renal dose and a plurality of combinations of one adjustable value for a flow of a blood pump and one adjustable value for a flow of a dialysis liquid pump, wherein the second input interface is used to select a combination from the plurality of combinations displayed by the user; and
give the adjustable value for the blood pump and the adjustable value for the dialysis liquid pump of a selected combination via the output interface.

11. The dialysis apparatus according to claim 10, wherein the dialysis apparatus comprises a hemodialysis apparatus or a hemofiltration apparatus or hemodiafiltration apparatus for chronic renal replacement therapy or continuous renal replacement therapy.

12. A system comprising
a dialysis apparatus and a computer system for setting adjustable values of the dialysis apparatus, the computer system provided separate from the dialysis apparatus and comprising:
a first input interface;
a second input interface;
an output interface; and
a display device;
a calculation device programmed to:
use the first input interface to read a target value of a renal dose as a parameter value for a treatment of a patient using the dialysis apparatus in order to display to a user in a graphic, via the display device, a selection range that is determined by the calculation device taking into account a read target value of the renal dose and a plurality of combinations of one adjustable value for a flow of a blood pump and one adjustable value for a flow of a dialysis liquid pump, wherein the second input interface is used to select a combination from the plurality of combinations displayed by the user; and
give the adjustable value for the blood pump and the adjustable value for the dialysis liquid pump of a selected combination via the output interface.

13. A method for setting adjustable values of a blood treatment apparatus comprising a computer system that comprises:
- a first input interface;
- a second input interface;
- an output interface; and
- a display device;
- a calculation device programmed to:
  - use the first input interface to read a target value of a renal dose as a parameter value for a treatment of a patient using the blood treatment apparatus in order to display to a user in a graphic, via the display device, a selection range that is determined by the calculation device taking into account a read target value of the renal dose and a plurality of combinations of one adjustable value for a flow of a blood pump and one adjustable value for a flow of a dialysis liquid pump, wherein the second input interface is used to select a combination from the plurality of combinations displayed by the user; and
  - give the adjustable value for the blood pump and the adjustable value for the dialysis liquid pump of a selected combination via the output interface wherein the method comprises:
- providing the computer system;
- reading the target value for the renal dose as the parameter value for the treatment of the patient via the blood treatment apparatus or entering the parameter value via the first input interface;
  - displaying the selection range in the graphic for the attention of the user via the display device;
- selecting of the combination of the plurality of combinations displayed by the user via the second input interface; and
- giving the adjustable value for the blood pump and the adjustable value for the dialysis liquid pump of the selected combination via the output interface.

14. The method according to claim 13, further comprising displaying for the attention of the user, the adjustable value for the blood pump and of the adjustable value for the dialysis liquid pump of the selected combination via the display device.

15. The method according to claim 13, further comprising:
- controlling or regulating the blood treatment apparatus based on the adjustable value for the blood pump and on the adjustable value for the dialysis liquid pump of the selected combination.

* * * * *

UNITED STATES PATENT AND TRADEMARK OFFICE
CERTIFICATE OF CORRECTION

| | | |
|---|---|---|
| PATENT NO. | : 12,409,256 B2 | Page 1 of 1 |
| APPLICATION NO. | : 17/775680 | |
| DATED | : September 9, 2025 | |
| INVENTOR(S) | : Juergen Klewinghaus | |

It is certified that error appears in the above-identified patent and that said Letters Patent is hereby corrected as shown below:

In the Claims

Claim 1
Column 13, Line 31, after "interface;" delete "and".
Column 13, Line 32, after "device;" insert --and--.

Claim 7
Column 14, Line 1, after "according" insert --to--.

Claim 10
Column 14, Line 18, after "interface;" delete "and".
Column 14, Line 19, after "device;" insert --and--.

Claim 12
Column 14, Line 49, after "interface;" delete "and".
Column 14, Line 50, after "device;" insert --and--.

Claim 13
Column 15, Line 6, after "interface;" delete "and".
Column 15, Line 7, after "device;" insert --and--.
Column 15, Line 24, after "interface" insert --;--.

Signed and Sealed this
Fourth Day of November, 2025

John A. Squires
*Director of the United States Patent and Trademark Office*